United States Patent
Allberg

(10) Patent No.: US 7,615,740 B2
(45) Date of Patent: Nov. 10, 2009

(54) SYRINGE-SHAPED DOSE CALIBRATION SOURCE STANDARD

(75) Inventor: Keith C. Allberg, Weare, NH (US)

(73) Assignee: Radqual, LLC, Concord, NH (US)

( * ) Notice: Subject to any disclaimer, the term of this patent is extended or adjusted under 35 U.S.C. 154(b) by 0 days.

(21) Appl. No.: 11/485,872

(22) Filed: Jul. 13, 2006

(65) Prior Publication Data

US 2007/0235641 A1    Oct. 11, 2007

Related U.S. Application Data

(60) Provisional application No. 60/791,161, filed on Apr. 11, 2006.

(51) Int. Cl.
*G01D 18/00* (2006.01)
(52) U.S. Cl. .................................. 250/252.1
(58) Field of Classification Search ............. 250/252.1
See application file for complete search history.

(56) References Cited

U.S. PATENT DOCUMENTS

| | | | |
|---|---|---|---|
| 4,333,010 A | 6/1982 | Miller | |
| 4,401,108 A | 8/1983 | Galkin et al. | |
| 4,430,258 A * | 2/1984 | McFarland et al. | 252/644 |
| 4,506,155 A | 3/1985 | Suzuki et al. | |
| 6,251,059 B1 | 6/2001 | Apple et al. | |
| 2002/0156338 A1 | 10/2002 | Menuhr | |
| 2004/0260143 A1 | 12/2004 | Reilly et al. | |
| 2005/0029465 A1 | 2/2005 | Lemer | |
| 2005/0047114 A1 | 3/2005 | Harrell et al. | |
| 2005/0107698 A1 | 5/2005 | Powers et al. | |

FOREIGN PATENT DOCUMENTS

EP    1416297    6/2004

OTHER PUBLICATIONS

Biodex—http://www.biodex.com/radio/dosecal/dose_242.htm#description.*
U.S. Appl. No. 60/791,161, filed Apr. 11, 2006, Allberg.
*Atomlab 100 Plus Dose Calibrator*, http://www.biodex.com/radio/dosecal/dose_265feat.htm., downloaded Jun. 21, 2006, copyright 2003.

* cited by examiner

*Primary Examiner*—Constantine Hannaher
*Assistant Examiner*—Marcus H Taningco
(74) *Attorney, Agent, or Firm*—Fay Sharpe LLP; Ann M. Skerry

(57) ABSTRACT

A dose calibrator source standard includes a container comprising a cylindrical barrel and a support member which extends radially outward of the cylindrical barrel. A radioactive source-containing material is sealed within the container. The radioactive source-containing material comprising a radionuclide dispersed within a matrix material.

20 Claims, 4 Drawing Sheets

SYRINGE-SHAPED DOSE CALIBRATION SOURCE STANDARD

This application claims the priority of U.S. Provisional Application Ser. No. 60/791,161, filed Apr. 11, 2006, entitled DOSE CALIBRATOR SYRINGE DESIGN, the disclosure of which is incorporated herein in its entirety, by reference.

BACKGROUND

The present exemplary embodiment relates to radiopharmaceuticals. It finds particular application in conjunction with a dose calibrator or radioisotope calibrator, and will be described with particular reference thereto. However, it is to be appreciated that the present exemplary embodiment is also amenable to other like applications.

A dose calibrator (radioisotope calibrator) is a device used in nuclear medicine that measures the total energy of a specific radionuclide in units of Curies (Ci), millicuries (mCi), or microcuries (μCi). It includes a hollow, lead-shielded cylinder, into which radionuclides are lowered for measurement. Such devices can be programmed for specific radioisotopes, or adjusted for isotopes not preprogrammed. A dose calibrator is commonly used to obtain measurements of the total radioactivity of isotopes prior to administration to patients undergoing nuclear medicine diagnostic imaging procedures or radioisotope therapy procedures. Regulatory authorities specify when a radioisotope dose calibrator will be used and the timing of required quality control checks (constancy, accuracy, linearity, and geometrical dependence).

Currently, a dose calibration source standard is used for calibration of the dose calibrator. The calibration source includes a cylindrical vial comprising a predetermined amount of the radionuclide to be calibrated, together with a decay calendar, which allows a user to determine the amount of radionuclide present in the source at the time of testing. The current dose calibration source standards are designed to closely approximate the geometry of unit dose radiopharmaceuticals dispensed in vials by radiopharmacies (specifically, a Tc-99$^m$ generator elution vial, of 30 cc maximum volume) and may therefore only partially meet the standards implied in CEI-IEC 61145 "Calibration and Usage of Ionization Chamber Systems for Assay of Radionuclides;" CEI-IEC 1303 "Medical Electrical Equipment—Radionuclide Calibrators—Particular Method of Describing Performance;" ANSI N42.13-1986 "Calibration and Usage of 'Dose Calibrator' Ionization Chambers for the Assay of Radionuclides;" and 10 CFR 35.50 "Possession, Use, Calibration, and Check of Dose Calibrators."

Nuclear medicine practitioners generally administer radiopharmaceuticals using a syringe. The practitioner places the syringe containing the radiopharmaceutical into the pre-calibrated dose calibrator to assay its content. The syringe has a different body shape from that of the calibration vials used as calibration standards and, due to the shape of the syringe and configuration of the dose calibrator, is positioned in the dose calibrator with the syringe body in a different location from the vial.

BRIEF DESCRIPTION

In one aspect of the invention, a dose calibrator source standard includes a container comprising a cylindrical barrel and a support member which extends radially outward of the cylindrical barrel. A radioactive source-containing material is sealed within the container, the radioactive source-containing material comprising a radionuclide dispersed within a matrix material.

In another aspect, a combination of a dose calibrator source standard and an ion chamber syringe scoop is provided. The dose calibrator source standard includes a barrel. A support member extends radially outwardly of the barrel. A radioactive source-containing material is sealed within the barrel. The radioactive source-containing material includes a radionuclide dispersed within a matrix material. The syringe scoop includes a syringe shelf configured for supporting an associated syringe thereon, the syringe shelf configured for engaging the support member.

In another aspect, a method of calibrating a dose calibrator includes providing a dose calibrator source standard comprising a container comprising a cylindrical barrel and a support member that extends radially outward of the cylindrical barrel and a radioactive source-containing material sealed within the container. One of a vial calibration mode and a syringe calibration mode is selected. When the vial calibration mode is selected, the dose calibrator source standard is supported in a cup of a scoop. When the syringe calibration mode is selected, the dose calibrator source standard is supported by the support member on a shelf of the scoop. The shelf is spaced from the cup. The scoop and dose calibrator source standard are inserted into the dose calibrator. A measure of the radiation emitted from the dose calibrator source standard is recorded.

In another aspect, a dose calibrator source standard includes a container comprising a cylindrical barrel closed by a closure member, and a support member defined by one of the barrel and the closure member. The support member extends radially outward of the cylindrical barrel adjacent a first end of the barrel. The container defines an interior. The barrel includes a planar base at a second end, for supporting the dose calibrator thereon, and a sidewall having a length which is at least twice a diameter of the base for mimicking dimensions of a barrel of a syringe. A radioactive source-containing material is sealed within the container interior, the radioactive source-containing material comprising a radionuclide dispersed within a matrix material.

DETAILED DESCRIPTION

Aspects of the exemplary embodiment relate to a dose calibrator source standard which is designed to closely approximate the geometry of unit dose radiopharmaceuticals dispensed in syringe form which meets the above-mentioned CEI-IEC, ANSI, and CFR standards.

Current dose calibrator source standards are designed to approximate the geometry of a typical radiopharmaceutical multidose vial or radionuclide generator elution vial (10 milliliters volume and 30 milliliters volume, respectively). While a cylindrical vial was adequate a number of years ago, the dispensing of radiopharmaceuticals in a syringe for unit dosing no longer provides dose calibrator source standards that approximate radioactivity volume or physical geometry of a typical syringe assay. The exemplary dose calibrator source standard is designed to provide a National Institute of Science and Technology traceable standard where the radioactivity volume and physical geometry of the body of a syringe is reproduced, which may also serve as a vial standard.

Figure 1:
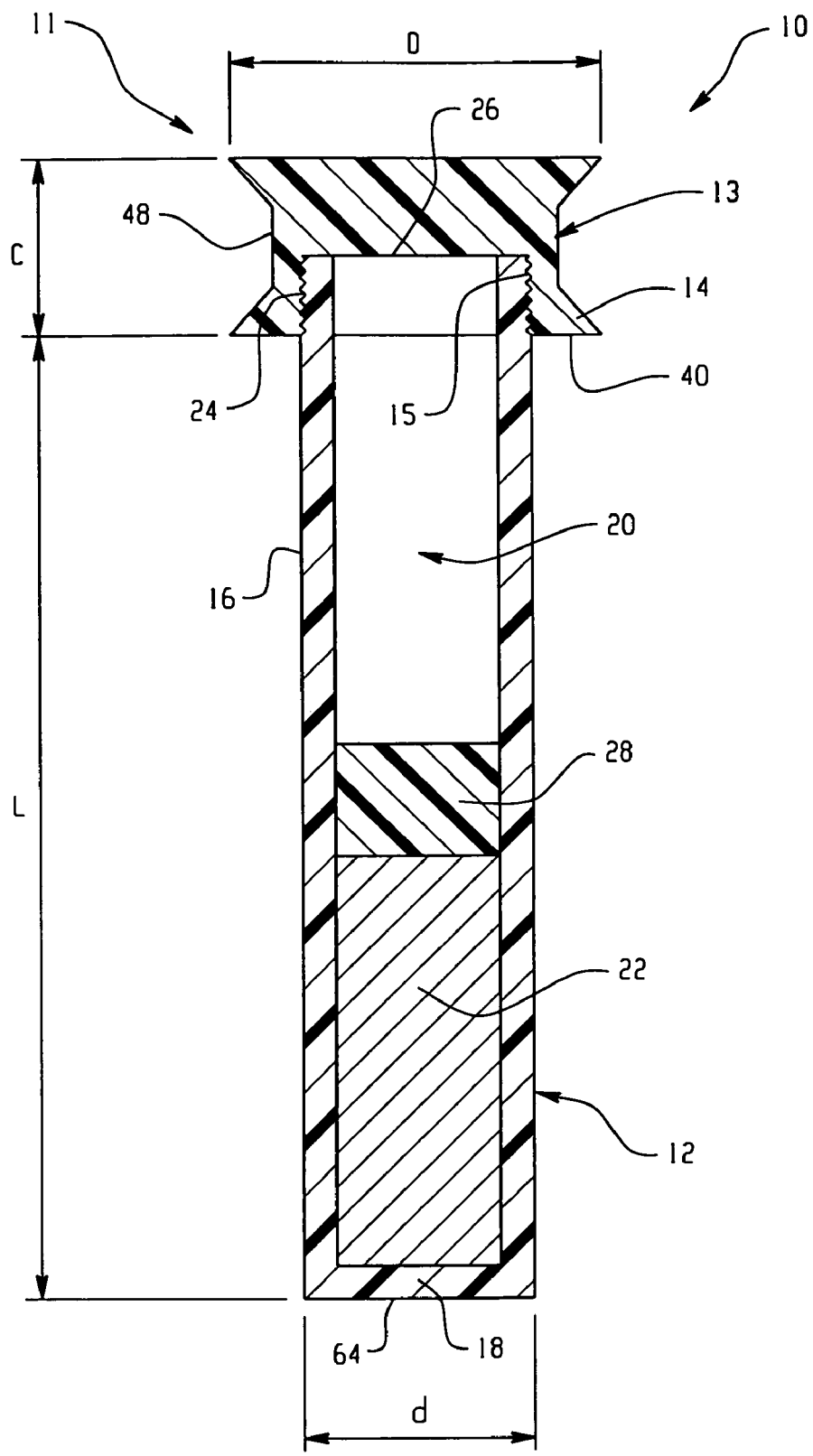
FIG. 1 is a side sectional view of a dose calibrator source standard according to a first aspect of the exemplary embodiment.

With reference to FIG. 1, a first embodiment dose calibrator source standard 10 according to the exemplary embodiment is illustrated. The source standard 10 includes a container 11 which includes a cylindrical encapsulation barrel 12 configured to mimic the barrel of a syringe and a closure member 13 mounted to the encapsulation barrel, which mimics the plunger of the syringe. The illustrated closure member 13 defines an enlarged diameter support member 14 in the form of a laterally extending annular flange and an interior socket 15. The encapsulation barrel 12 includes a cylindrical wall 16 of substantially uniform cross section which is closed at a lower end by a base 18. The base 18 may be integrally formed with the wall 16, for example by molding. The upper end of the barrel 12 is closed by the closure member 13 to define a sealed interior 20. A radioactive source-containing material 22 is sealed within the encapsulation barrel 12. The barrel 12 includes an exterior threaded portion 24 at an upper open end 26 which is configured for threadably engaging corresponding interior threads on the socket 15 of the closure member. A sealant material (not shown), may be applied to the threads to provide an airtight and tamper-resistant seal between the barrel 12 and the closure member 13. A void created between the radioactive source containing material 22 and the closure member 13 may be backfilled with an appropriate polymer matrix 28, such as epoxy, urethane, silicone, or other appropriate material. While FIG. 1 shows the interior having an air space above the matrix 28, it is contemplated that the entire interior space 20 above the radioactive material 22 may be backfilled with matrix 28, leaving no air space.

Figure 2:
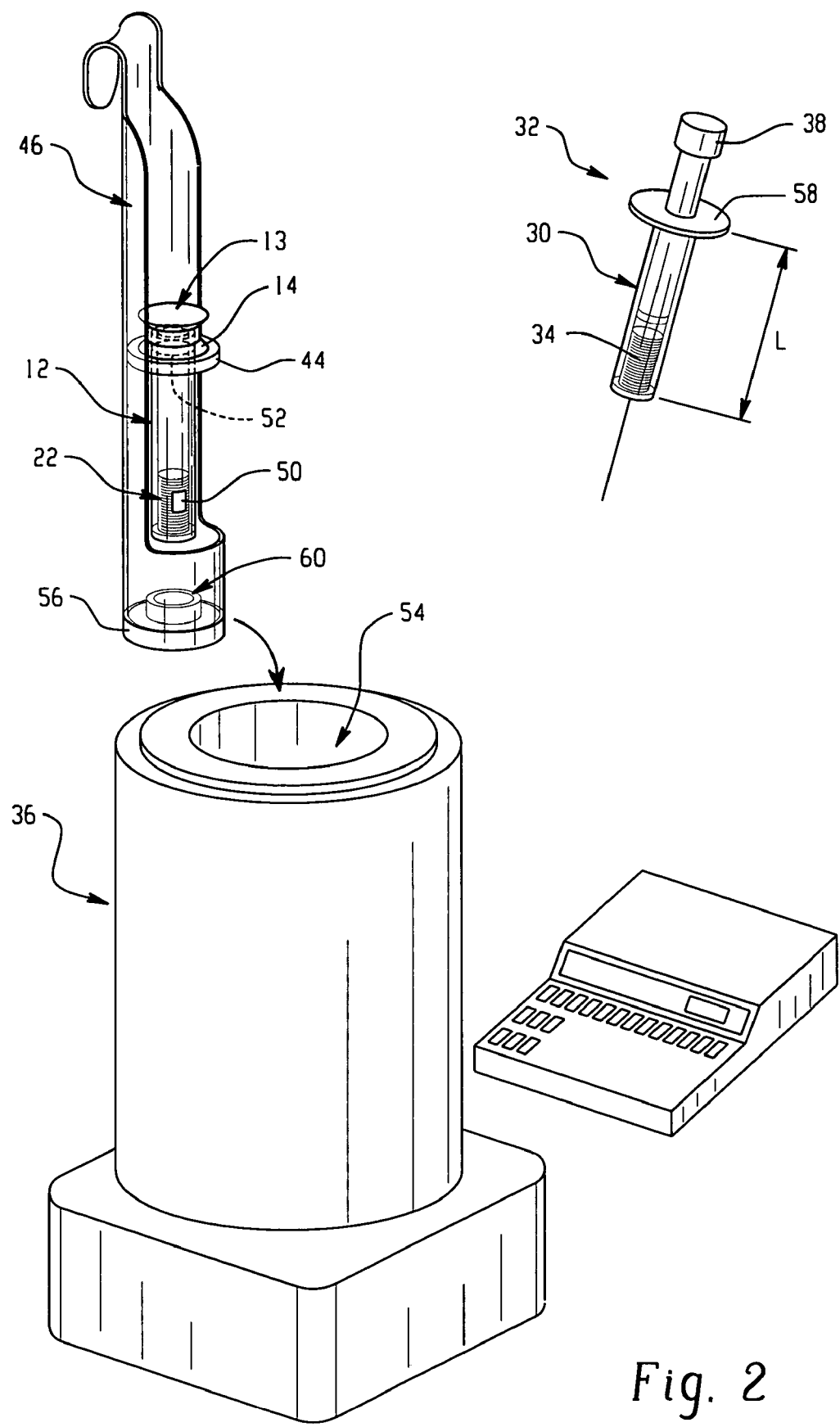
FIG. 2 is a perspective view of the dose calibrator source standard being lowered into a dose calibrator with a scoop and a syringe containing a radionuclide to be calibrated.
Figure 3:
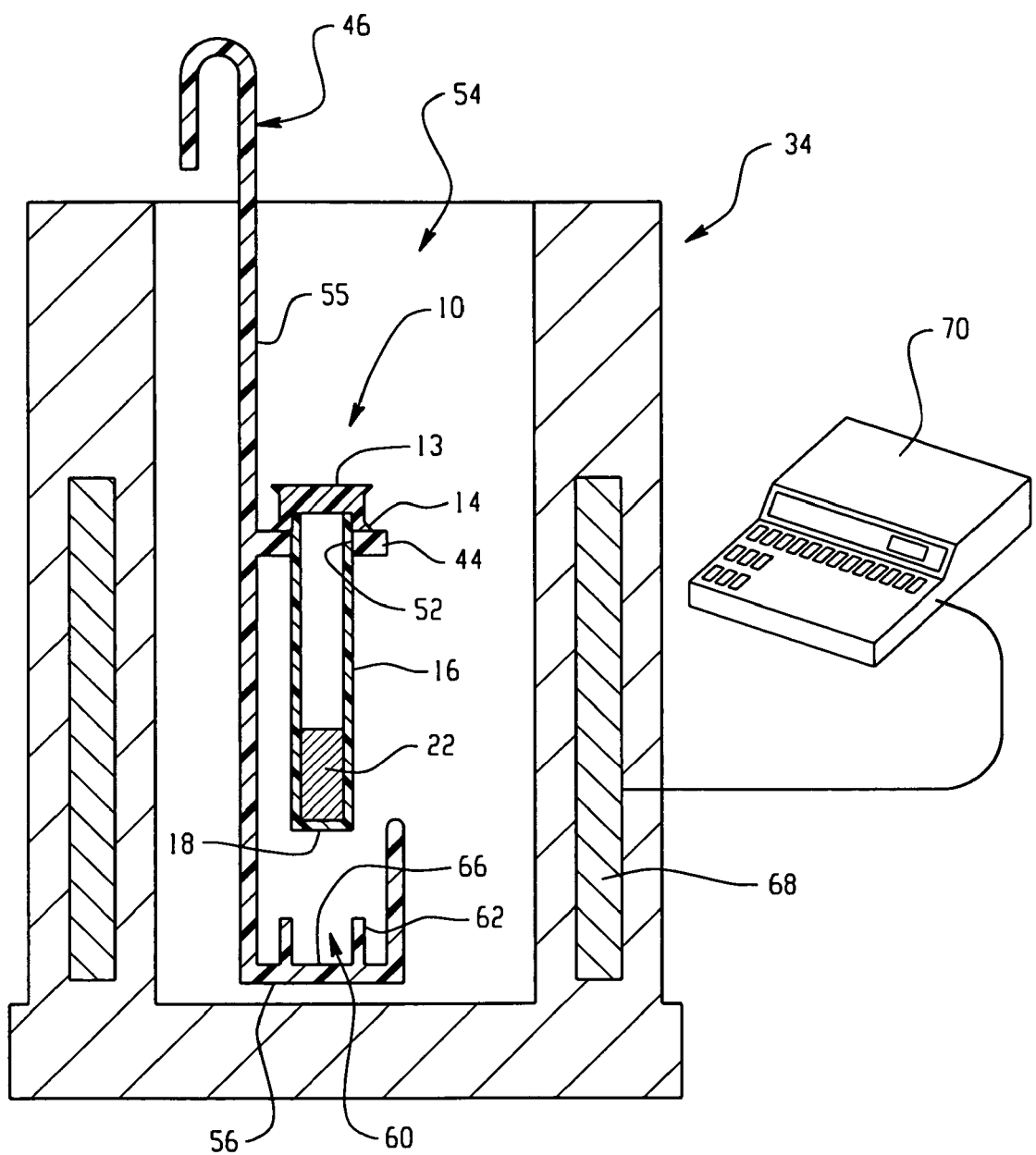
FIG. 3 is a side sectional view of the dose calibrator source standard, dose calibrator, and scoop of FIG. 2, during a calibration.

The encapsulation barrel 12 and closure member 13 may be formed from a plastic polymer, such as Lucite®, or a low Z material, such as aluminum or other material which is transmissive to substantially all radiation emitted from the source. The barrel 12 has an outer diameter d and length L (as measured from the base to support member) similar to that of a barrel 30 of a syringe 32 containing a radiopharmaceutical 34 which is to be tested in a dose calibrator 36 of the type shown in FIGS. 2 and 3. In general the sidewall 16 has a length L which is at least twice a diameter d of the base 18. For example, the diameter d and length L may be within ±10% of the actual syringe dimensions, e.g., within ±5%, or identical thereto. The radioactive nuclide-containing material 22 thus occupies dimensions and a volume comparable to that of the radiopharmaceutical liquid 34 to be tested.

In one embodiment, the outer barrel diameter d may be up to about 2.5 cm (1 inch) and the barrel length L up to about 10 cm (4 inches). The volume of the interior 20 may be from about 3 to about 10 cm³. The closure member 13 may have a height C and/or other dimensions which are similar to that of a plunger 38 of the syringe 32 for ease of handling although in general, the dimensions of the closure member are not critical. In operation, the illustrated support member 14 extends radially outwardly from the barrel wall 16 to define an annular surface 40 suitable for seating on a syringe shelf 44 of an ion chamber syringe scoop 46 of the type shown in FIGS. 2 and 3. While in one embodiment, surface 40 is annular, it is also contemplated that the surface may be of any suitable configuration for resting on the shelf 44. For example, the surface 40 may be defined by two (or more) radially extending wings. The surface 40 may extend about 0.3 cm to about 2 cm from the barrel 12, e.g., at least about 0.5 cm. The exact dimension may depend on the configuration of the scoop 46. The illustrated support member 14 includes an annular generally concave cavity 48, spaced from the support surface, for ease of transporting the dose standard 10.

While in the illustrated embodiment, the support member 14 is defined by the closure member 13, in alternate embodiments, the support member may be defined by the barrel 12, e.g., by being integrally formed therewith, for example as a lip The radioactive source-containing material 22 may include one or more radionuclides encapsulated in a suitable solid matrix material. Exemplary nuclides include gamma radiation emitters, such as sodium 22 (Na-22), cobalt 57 (Co-57), cobalt 60 (Co-60), germanium 68 (Ge-68), barium 133 (Ba-133), thallium 204 (TI-204), and cesium 137 (Cs-137) in appropriate quantities for serving as a standard for calibration. The matrix material may comprise an epoxy, silicone, urethane, ceramic, or similar type of matrix material in which the radionuclide may be uniformly dispersed.

To form the source standard 10, appropriate quantities of a radionuclide and a liquid polymer composition are mixed to disperse the radionuclide uniformly. The polymer composition may include a polymer resin together with accelerators, crosslinking agents, and the like which cause the polymer to harden when cured (e.g., by UV-curing or an ambient cure). The liquid radionuclide/polymer composition is placed in the barrel 16 and cured to form a solid 22. The barrel 16 may then be backfilled with polymer matrix material, which is also cured. The barrel is then sealed to the closure member 13, for example, by placing a small amount of the polymer matrix material around the threads 24 and threadably connecting the closure member 13 to the barrel 12. The assembled source standard 10 is then calibrated e.g., against a traceable National Institute of Standards (NIST) solution. A custom decay calendar may then be derived and affixed by means of a label 50 to the source standard 10 or to a shielding container in which the source standard 10 is shipped and stored.

The source standard can be used in two different calibration modes. To calibrate the dose calibrator 36 for use with syringes (first mode), the source standard 10 is supported on the syringe shelf 44 of a suitably configured syringe scoop 46. The scoop shelf 44 engages the support member surface 40. In particular, the scoop shelf 44 has a generally centrally positioned circular aperture 52 therein which is sized to accommodate the barrel 12 therethrough but which is smaller than the maximum diameter D of the support surface 40. The scoop 46 is then lowered into an ion chamber 54 of the dose calibrator 36 by a vertically extending handle 55. The shelf 44 of the scoop is vertically spaced along the handle from a base 56 of the scoop by a sufficient distance such that the syringe 30 can subsequently be accommodated by the scoop while being supported with a lip 58 of the syringe barrel resting on the shelf 44. The illustrated scoop base 56 includes an upwardly open vial cup 60 comprising a cylindrical wall 62 of suitable diameter to receive a conventional cylindrical vial source standard (not shown) therein. The exemplary base 18 of the source standard 10 is sized to fit within the vial cup 54 and has a planar lower surface 64 whereby the source standard 10 can rest on a correspondingly sized planar base surface 66 of the vial cup 60 with the source standard 10 in an upright position (second mode). In this way, the source standard 10 can be used for calibrating the dose calibrator 34 for syringes (when suspended on the shelf 44), or for vials (when seated in the cup 60), simulating, for example, a 10 cc multidosing vial. In both cases, the radiation source-containing material 22 is correctly positioned so as to be in a comparable location in the ion chamber 54 of the dose calibrator 34 to the actual dose of radiopharmaceutical 34 in the vial or syringe 32. The radiation emitted by the source standard 10 is detected by a radiation detector 68 and a measure of the radiation, such as the amount of radiation emitted per unit time, is recorded on suitable instrumentation 70.

The exemplary source standard 10 thus described meets or exceeds the American National Standards Institute (ANSI) safety classification of 97C22312 as described in Publication ANSI/HPS N43.6-1997 "Sealed Radioactive Source—Classification."

The source standard 10 may be color-coded for easy identification, e.g., as follows:

| | | | |
|---|---|---|---|
| Green: Cs-137 | Red: Co-57 | Blue: Co-60 | Yellow: Na-22 |
| Black: Ba-133 | White: Ge-68 | Orange Tl-204 | |

Figure 4:
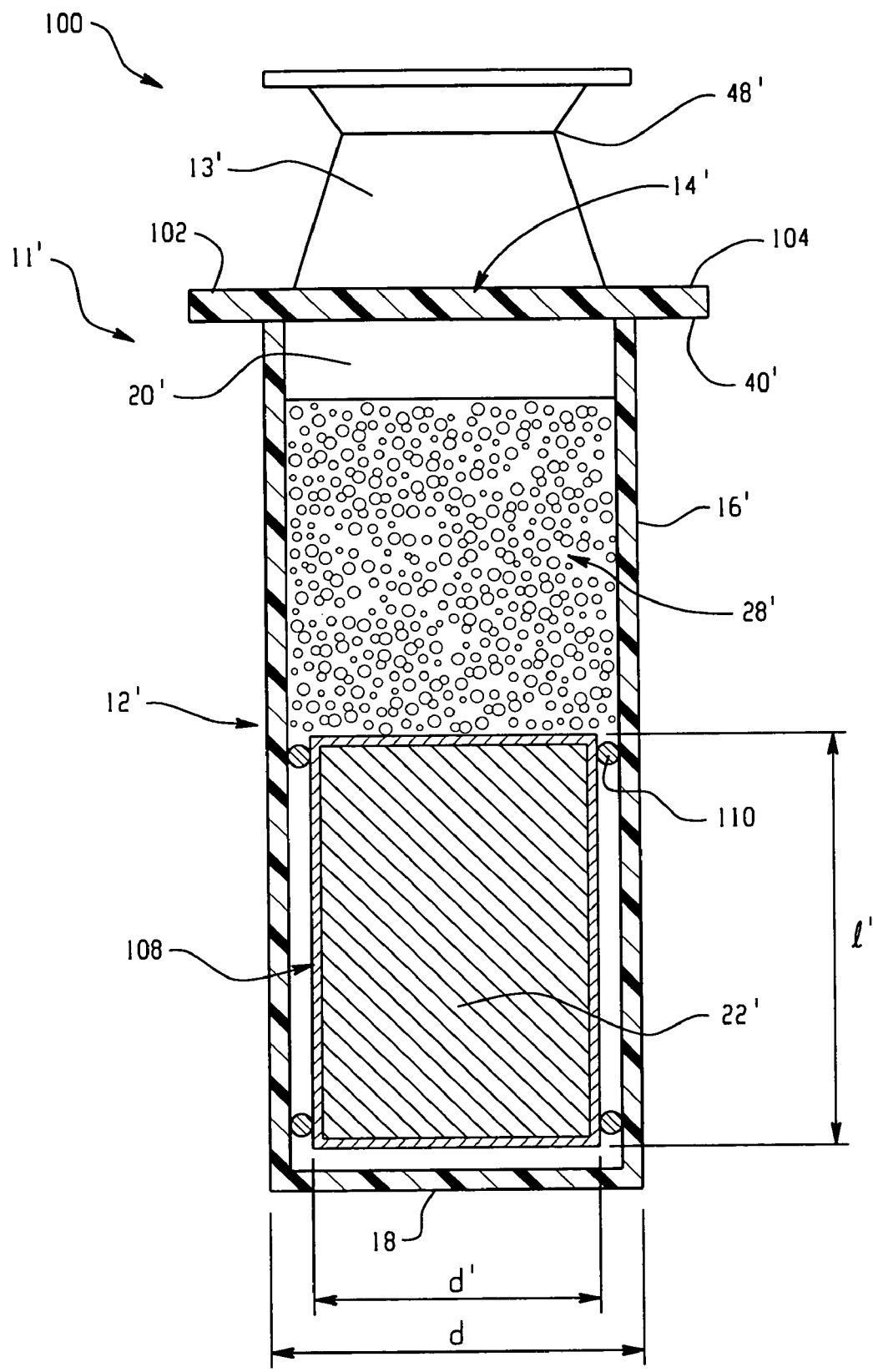
FIG. 4 is a side sectional view of a dose calibrator source standard according to a second aspect of the exemplary embodiment.

FIG. 4 illustrates another embodiment of a source standard 100 which may be similarly configured to source standard 10, except as noted. In this embodiment, similar elements are identified by a primed suffix (') and new elements are accorded new numbers. In this embodiment, a support surface 40' is defined by two finger wings 102, 104, which extend approximately 1-2 cm beyond the barrel diameter d. The wings may be integrally formed with the barrel 12' or with a cover member 13' in the form of a mock plunger, which seals the open end of the barrel 12'. The finger wings 102, 104 extend in opposite directions to support the source standard 10 in existing ion chamber scoops, such as scoop 46.

The embodiment of FIG. 4 provides a double encapsulation for the source material 22. An outer encapsulation is provided by the barrel and mock plunger 13', while inner encapsulation is provided by a cylindrical housing 108 made of a plastic polymer or low Z material, such as aluminum. The housing 108 is sized to fit within the interior 20' of the barrel. For example, the housing 108 is no greater than about 2 cm (0.8 inches) in diameter d' and no greater than about 4 cm (about 1.50 inches) in length l' and may be centered in the barrel with the use of o-rings 110 secured around the housing prior to insertion into the outer barrel 12'. The radiation source-containing material is sealed within the housing 108. This embodiment provides for double encapsulation of the matrix 22 with metal, plastic, or a combination of both. However, it is also contemplated that the outer container 11' need not be sealed and that the radiation source-containing material may be sealed within the container 11' by virtue of the inner housing 108.

The void created between the radioactive source encapsulation and the mock plunger may be backfilled with an appropriate matrix 28 such as epoxy, urethane, silicone, or other appropriate material.

In this embodiment, the outer container 11' may be formed from a hollowed out rod of material which is machined exteriorly to define the mock plunger. The container 11' is sealed at the end to form a base 18' after insertion of the inner housing 108 containing radioactive material.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A dose calibrator source standard comprising:
   a container comprising a cylindrical barrel and a support member which extends radially outward of the cylindrical barrel; and
   a radioactive source-containing material sealed within the container, the radioactive source-containing material comprising a radionuclide dispersed within a matrix material.

2. The dose calibrator source standard of claim 1, wherein the container includes a closure member which is threadably mounted to the barrel.

3. The dose calibrator source standard of claim 1, wherein the support member is integrally formed with a closure member which closes an open end of the barrel.

4. The dose calibrator source standard of claim 1, wherein the barrel includes a planar base configured for unaided support of the dose calibrator source standard in an upright position thereon.

5. The dose calibrator source standard of claim 1, wherein the support member and barrel in cooperation define a sealed interior chamber which houses the radioactive source-containing material.

6. The dose calibrator source standard of claim 1, wherein the support member and barrel in cooperation define an interior chamber.

7. The dose calibrator source standard of claim 1, wherein the support member is annular.

8. The dose calibrator source standard of claim 1, wherein the support member defines a surface configured for suspending the dose calibrator source standard on a shelf of an associated ion chamber syringe scoop.

9. The dose calibrator source standard of claim 1, wherein the barrel includes a base and a cylindrical wall, the base having a lower surface which is generally perpendicular to the side wall for supporting the dose calibrator source standard in an upright position thereon.

10. The dose calibrator source standard of claim 1, wherein the support member extends at least 0.3 cm from the barrel.

11. The dose calibrator source standard of claim 1, wherein the nuclide includes a gamma radiation emitter selected from the group consisting of sodium 22, cobalt 57, cobalt 60, germanium 68, barium 133, thallium 204, cesium 137,and combinations thereof.

12. In combination, a dose calibrator source standard and ion chamber syringe scoop comprising:
   a dose calibrator source standard comprising a barrel, a support member extending radially outwardly of the barrel, the barrel including a base and a sidewall substantially perpendicular to the base, and a radioactive source-containing material sealed within the barrel, the radioactive source-containing material comprising a radionuclide dispersed within a matrix material; and
   a syringe scoop comprising:
      a syringe shelf configured for supporting an associated syringe thereon, the syringe shelf configured for engaging the support member to suspend the dose calibrator source standard in the location of a syringe of a radiopharmaceutical to be calibrated; and
      a vial cup, spaced from the shelf, for receiving an associated vial containing a source of radiation and wherein the base of the dose calibrator source standard is sized for receipt within the vial cup to seat the dose calibrator source standard in the location of a vial of a radiopharmaceutical to be calibrated.

13. The combination of claim 12, wherein the barrel is of similar dimensions to a barrel of the associated syringe.

14. The combination of claim 12, wherein the syringe shelf supporting member defines an aperture which receives the barrel therethrough.

15. A system comprising the combination of claim 12 and a dose calibrator which receives the scoop therein.

16. A method of calibrating a dose calibrator comprising:
providing a dose calibrator source standard comprising a container comprising a cylindrical barrel and a support member which extends radially outward of the cylindrical barrel and a radioactive source-containing material sealed within the container;
selecting one of a vial calibration mode and a syringe calibration mode;
when the vial calibration mode is selected, supporting the dose calibrator source standard in a cup of a scoop;
when the syringe calibration mode is selected, supporting the dose calibrator source standard by the support member on a shelf of the scoop, the shelf being spaced from the cup;
inserting the scoop and dose calibrator source standard into the dose calibrator; and
recording a measure of the radiation emitted from the dose calibrator source standard.

17. The method of claim 16, wherein the supporting of the dose calibrator source standard by the support member on the shelf includes resting the support member on the shelf with the barrel extending through an aperture in the shelf.

18. The method of claim 16, wherein the supporting the dose calibrator source standard in the cup includes supporting a planar base of the barrel on a planar support surface of the cup.

19. The method of claim 16, wherein,
in the vial calibration mode, the radioactive source-containing material is positioned within the dose calibrator in the location of an associated vial of a radiopharmaceutical to be calibrated with the dose calibrator; and
in the syringe calibration mode, the radioactive source-containing material is positioned within the dose calibrator in the location of a syringe of a radiopharmaceutical to be calibrated with the dose calibrator.

20. A dose calibrator source standard comprising:
a container comprising a cylindrical barrel closed by a closure member, and a support member defined by one of the barrel and the closure member, the support member extending radially outward of the cylindrical barrel adjacent a first end of the barrel and configured for suspending the dose calibration source standard from a shelf of an associated scoop whereby the dose calibration source standard serves as a calibration source for a syringe, the container defining an interior, the barrel including a planar base at a second end, for supporting the dose calibrator thereon and a sidewall having a length which is at least twice a diameter of the base for mimicking dimensions of a barrel of a syringe, the base being configured for receipt in the cup of the scoop, whereby the dose calibration source standard serves as a calibration source for a vial; and
a radioactive source-containing material sealed within the container interior, the radioactive source-containing material comprising a radionuclide dispersed within a matrix material.

* * * * *